United States Patent [19]

Krull et al.

[11] Patent Number: 5,302,677
[45] Date of Patent: Apr. 12, 1994

[54] ALKENYLAMINOALKANE-1,1-DIPHOSPHONIC ACID DERIVATIVES AND COPOLYMERS THEREOF WITH UNSATURATED CARBOXYLIC ACIDS

[75] Inventors: Matthias Krull, Bad Soden am Taunus; Christoph Naumann, Niedernhausen; Herrmann Hoffmann, Kelkheim, all of Fed. Rep. of Germany

[73] Assignee: Hoechst Aktiengesellschaft, Frankfurt, Fed. Rep. of Germany

[21] Appl. No.: 37,256

[22] Filed: Mar. 26, 1993

[30] Foreign Application Priority Data

Mar. 28, 1992 [DE] Fed. Rep. of Germany ....... 4210296

[51] Int. Cl.$^5$ ............................................. C08F 230/02
[52] U.S. Cl. .................................. 526/240; 526/278; 526/271; 526/264; 526/287
[58] Field of Search ................................ 526/278, 240

[56] References Cited

U.S. PATENT DOCUMENTS 4,678,840  7/1987  Fong et al. ........................ 525/340
5,126,418  6/1992  Porz et al. ........................ 526/278

FOREIGN PATENT DOCUMENTS 0437843  7/1991  European Pat. Off. .
50-72987  6/1975  Japan .
54-135724  10/1979  Japan .

OTHER PUBLICATIONS

Ragnetti, M. *Tenside, Surfactants, Detergents* 26, 30–34 (1989) Note English abstract on p. 30.
Lancaster et al, *Polym. Lett.* 14, 549–554 (1976).

*Primary Examiner*—Joseph L. Schofer
*Assistant Examiner*—Mark Nagumo
*Attorney, Agent, or Firm*—Connolly and Hutz

[57] ABSTRACT

The invention relates to alkenylaminoalkane-1,1-diphosphonic acid derivatives of the formula I

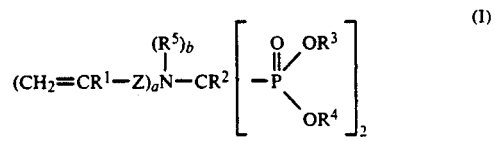

in which $R^1$ to $R^5$, a, b, and Z have the meaning given in the description and to processes for their preparation. The invention furthermore relates to copolymers comprising 0.1–50 mol %, preferably 1–15 mol %, of at least one alkenylaminoalkane-1,1-diphosphonate unit of the formula I and 99.9–50 mol %, preferably 99–85 mol %, of at least one carboxylic acid unit of the formula II $$R^6R^7C=CR^8Y \qquad (II)$$

in which $R^6$, $R^7$, $R^8$ and Y have the meaning given in the description and to processes for their preparation. These copolymers are used as scale inhibitors, as alkaline earth metal and heavy metal complexing agents and/or sequestering agents and as builders or co-builders in detergents.

15 Claims, No Drawings

ALKENYLAMINOALKANE-1,1-DIPHOSPHONIC ACID DERIVATIVES AND COPOLYMERS THEREOF WITH UNSATURATED CARBOXYLIC ACIDS

When oil, water and gas are extracted from underground formations, mixing of incompatible aqueous media, and changes in temperature and pressure may result in scale formation. Scale formation can lead, inter alia, to blocking of formations, drilling holes, extraction pipes and pipelines and to stuck pumps and valves and thus cause loss of production and substantial repair costs.

To prevent scale formation, i.e. precipitation of sparingly soluble alkaline earth metal salts, on the one hand, high-molecular-weight polycarboxylic acids (preferably against alkaline earth metal sulfate) and, on the other, low-molecular-weight polyelectrolytes, such as aminomethylenephosphonic acids (preferably against alkaline earth metal carbonate) are added to saline waters in less than stoichiometric amounts in the range from 1 to 100 ppm. It is believed that this so-called threshold effect is caused by absorption of the polyelectrolyte on the crystalline surfaces, which disturbs or prevents further crystal growth.

Owing to their good calcium and heavy metal binding power, aminomethylenephosphonic acids (e.g. ®Dequest, Monsanto) and other low-molecular-weight polyelectrolytes, such as, for example, EDTA and triphosphates, also have wide practical application in bleach washing. The heavy metals present reduce the shelf life of detergent formulations and damage the fibers during bleaching. Likewise, high-molecular-weight polycarboxylic acids are of great importance as co-builders in phosphate-free and phosphate-reduced detergents (Ragnetti; Tenside, Surfactants, Detergents 1989,26,30). It is assumed that they transport water-soluble-metal ions, in particular calcium ions, from the aqueous detergent liquor into the water-soluble zeolites.

Copolymers of alkenylaminomethylenephosphonic acids with unsaturated carboxylic acids which are suitable as complexing agents, in particular in detergents, as builders, peroxide stabilizers and as granulating aids for bleaching activators and as scale inhibitors having anticorrosive action in crude oil production are disclosed in U.S. Pat. No. 5,126,418.

JP-A-54/135,724 describes a process for the preparation of aminomethylenephosphonic esters and antacid hydrolysis thereof to give the free phosphonic acids, for example synthesis of tetraethyl N-diallylaminomethylenediphosphonate and the corresponding acid.

JP-A-50/72,987 describes homo- and copolymerization of diallylaminomethylenephosphonic acid with ethylenically unsaturated monomers to give high-molecular-weight (co) polymers. The polymerization of diallylammonium salts produces barely branched polymers containing piperidinium groups (Lancaster et al.; Polym. Lett. 1976, 14,549).

Surprisingly, it has now been found that alkenylaminoalkane-1,1-diphosphonates can be copolymerized with unsaturated carboxylic acids and the copolymers obtained combine the known properties of the different monomers in a single compound.

The present invention relates to alkenylaminoalkane-1,1-diphosphonates of the formula

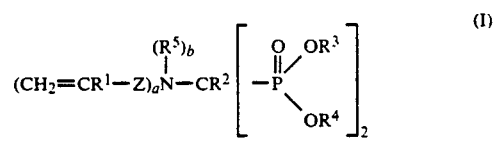

in which
R[1] is hydrogen or methyl,
R[2] is hydrogen or $C_1$-$C_{10}$-alkyl,
R[3] is $C_1$-$C_4$-alkyl or phenyl
R[4] is hydrogen or a cation, preferably sodium, potassium or ammonium,
R[5] is $C_1$-$C_{22}$-alkyl, $C_3$-$C_{22}$-alkenyl, preferably propenyl,
Z is $C_1$-$C_3$-alkylene and
a is 1 or 2, b is 0 or 1, a+b is 2.

The alkenylaminoalkane-1,1-diphosphonates according to the invention of the formula I are advantageously obtained by mixing a diester of phosphorous acid, an alkyl orthoformate and an alkenylamine with the addition of a catalyst, such as boron trifluoride etherate, if desired in a solvent, and reaction at temperatures in the range from 50° to 150° C. while distilling off the alcohol formed, followed by alkaline hydrolysis.

Usually, 0.5 to 2.0 mol, preferably 1.0 to 1.3 mol, of alkyl orthoformate and 1.5 to 3.0 mol, preferably 2.0 to 2.5 mol of the diester of phosphorous acid are reacted per mole of the amine in question.

Examples of suitable diesters of phosphorous acid are dialkyl esters with the $C_1$-$C_5$-alkyl, such as dimethyl ester, diethyl ester, diphenyl ester or alkylaryl ester, such as benzyl esters.

Preference should be given to amines whose boiling point is above the boiling point of the resulting alcohol, for example 3-methylamino-1-propene; 3-ethylamino-1-propene; 3-butylamino-1-propene;3-heptylamino-1-propene; 3-amino-1-butene; 4-amino-1-butene; 4-ethylamino-1-butene; 3-amino-2-methyl-1-propene; 3-methylamino-2-methyl-1-propene; diallylamine; dimethallylamine; 3-amino-1-pentene; 4-amino-1-pentene; 5-amino-1-pentene. Diallylamine is particularly preferred.

Suitable alkyl orthoformates are $C_1$-$C_4$-alkyl esters, in particular ethyl orthoformate.

Suitable solvents should have a boiling point above the boiling point of the resulting alcohol, toluene, xylene, dichlorobenzene, dimethyl formamide, dimethyl sulfoxide or nitrobenzene being preferably used.

The alkenylaminoalkanediphosphonic esters formed in the reaction described above are preferably hydrolyzed by addition of bases, such as sodium hydroxide solution, potassium hydroxide solution or ammonia water to give the compounds according to the invention of the formula I. Compared with hydrolysis using acid, such as hydrochloric acid, this alkaline hydrolysis has the advantage that formation of the toxic ethyl chloride does not take place. The salts of the compounds of the formula I formed during alkaline hydrolysis are obtained in high purity and yield and can be used directly for the copolymerization according to the invention. The addition of, preferably, equimolar amounts of acid, such as hydrochloric acid, converts the salts of the compounds of the formula I into the corresponding acids.

The invention furthermore relates to copolymers containing 0.1 to 50 Mol %, preferably 1 to 15 mol %, of at least one alkenylaminoalkane-1,1-diphosphonate unit of the formula I, in which $R^3$ is additionally hydrogen or a cation, such as sodium, potassium or ammonium, and 99.9 to 50 mol %, preferably 99 to 85 mol %, of at least one carboxylic acid unit of the formula $$R^6R^7C=CR^8Y \qquad (II)$$

in which $R^6$ and $R^7$, independently of one another, are hydrogen, phenyl or a group of the formula COOM, $R^8$ is hydrogen, methyl, phenyl or a group of the formula —$CH_2$—COOM, Y is a group of the formula —COOM— or $R^7$ and $R^8$ together are a $C_4$-alkylene radical, $R^7$ and Y together are a group of the formula —C(O)—O—C(O)— or $R^8$ and Y together are a group of the formula —$CH_2$—C(O)—O—C(O)— and in which M is hydrogen, $C_1$-$C_6$-alkyl or a cation, preferably sodium, potassium or ammonium, with the proviso that the monomers of the formula II carry one or two carboxylic acid units of the formula —C(O)—O— and contain 0 to 10 mol % of further ethylenically unsaturated monomers.

Representatives of suitable monomers of the formula I are diallylaminomethane-1,1-diphosphonic acid, diethyl disodium diallylaminomethane-1,1-diphosphonate, diethyl dipotassium diallylaminomethane-1,1-diphosphonate, N-methylallylaminomethane-1,1-diphosphonic acid, disodium N-methylallylaminomethane-1,1-diphosphonate.

Representatives of suitable monomers of the formula II are acrylic acid, methacrylic acid, maleic acid, maleic anhydride, itaconic acid and cinnamic acid and lower alkyl esters thereof, such as methyl acrylate and methyl methacrylate.

Apart from these monomers, further ethylenically unsaturated monomers, such as vinyl sulfonic acid, vinyl phosphonic acid, vinylpyrrolidone, N-vinylacetamide, acrylamide and N- and N,N-substitution products thereof, such as N-methylacrylamide or 2-acrylamido-2-methylpropanesulfonic acid, and also (meth)allyl compounds, such as, for example, (meth)allylamine, diallylamine and substitution products thereof, such as methyldiallylamine, octyldiallylamine, diallyldimethylammonium chloride, allylamino-bis(methylenephosphonic acid), allylaminobenzylidenephosphonic acid and diallylaminomethylene phosphonic acid can also be added to the polymerization system. The preferred amount of these comonomers is between 0.001 and 10 mol %.

The copolymers according to the invention are prepared by initially introducing compounds of the formula I as pure substances or contaminated with neutralization salts, such as sodium chloride or sodium sulfate, in water or in water-miscible organic solvents, preferably at 20° to 100° C., particularly preferably at 40° to 80° C., and compounds of the formula II and, if desired, further ethylenically unsaturated monomers and a radical chain initiator, for example ammonium peroxodisulfate, hydrogen peroxide or else tert.butyl hydroperoxide, are added in succession or simultaneously. The total monomer concentration is preferably 1 to 60 % by weight, particularly preferably 10 to 60 % by weight, relative to the total weight of the reaction batch. If the compounds of the formula I are water-insoluble alkenylaminoalkanediphosphonic acids, they can be made to dissolve by converting them into their alkaline metal salts or ammonium salts. Addition of the radical initiator which may be dissolved in a suitable solvent to the reaction vessel can take place simultaneously with or else after addition of the compounds of the formulae I and II.

A suitable molecular weight for the use according to the invention can be achieved by adding lower alcohols as solvents or else by addition of 0.001 to 30% by weight of a regulator, such as thioglycolic acid, thioethanol, ethanethiol, dodecanethiol, hypophosphorous acid, sodium bisulfite to the reaction batch. The molecular weight of the copolymers according to the invention is determined by their use, but is in principle not subject to any restriction. The preferred intrinsic viscosity K (determined by the method of Ubbelohde) of the polymers is, for example for use as scale inhibitor, between 10 and 100, in particular between 10 and 50.

Depending on their intended use, the viscous polymer solutions can be diluted, spray-dried and/or brought to the desired pH by means of bases.

The copolymers according to the invention combine the known properties of polyacrylates with those of aminoalkane-1,1-diphosphonic acid derivatives in a single compound. In saline formation waters, they lead to effective inhibition of deposit of both alkaline earth metal carbonate and alkaline earth metal sulfates. Furthermore, they can be used as alkaline earth metal and heavy metal complexing agents and/or sequestering agents in textile and paper bleaching and the like and, owing to their excellent dispersing effect on calcium carbonate, as builder and co-builder in detergents. They can be used in the machine cleaning, bottle cleaning, steam production, cooling water treatment and water treatment sectors for preventing scale formation.

The examples which follow are intended to illustrate the invention without limiting it.

EXAMPLES

Percentages are by weight unless stated otherwise. The water used in the examples is deionized. The intrinsic viscosity values K were determined by the method of Ubbelohde at 25° C. in water and a polymer concentration of 5% by weight. Polymerizations were carried out in a 1 l 5-neck flask equipped with flat ground-glass lid. The flasks are equipped with anchor stirrer, thermometer, reflux condenser, gas introduction tube and dropping funnel. The solutions initially introduced for polymerization were flushed with nitrogen.

EXAMPLE 1

Preparation of Diethyl Disodium Diallylaminomethane-1,1-Diphosphonate

The preparation of diallylaminomethane-1,1-diphosphonic ester is carried out according to JP-A-53/42,349. 160 g (0.42 Mol) of tetraethyl diallylaminomethane-1,1-diphosphonate are taken up in 300 ml of 33% sodium hydroxide solution, and the mixture is refluxed for 4 hours. The resulting colorless precipitate of the disodium salt is filtered off with suction, stirred in 50 ml of ethanol and again filtered off with suction. The colorless product is once again washed with 40 ml of methanol and dried, giving 58 g (38% of theory) of diethyl disodium diallylaminomethane-1,1- diphosphonate as a colorless powder having a melting point of greater than 300° C.

$^1$H-NMR (D$_2$O):=1.25 (t, 6H); 3.38 (t, 1H, $J_{P-C-H}$=24Hz); 3.50 (m, 4H); 3.93 (m, 4H; 5.08-5.40 (m. 4H): 5.68-6.10 (m. 2H).

$^{31}$P-NMR (D$_2$O):=18.4 ppm, $^2J_{P-H}$=$J_{P-C-H}$=23.65 Hz

EXAMPLE 2

Preparation of Diethyl Disodium Diallylaminomethane-1,1-Diphosphonate

The procedure of Example 1 is repeated, except that 160 g (0.42 mol) of diethyl diallylaminomethane-1,1-diphosphonate and 300 ml of 33% potassium hydroxide solution are used. In this manner, 66 g (38% of theory) of diethyl dipotassium diallylaminomethane-1,1-diphosphonate are obtained as a colorless powder having a melting point of greater than 300° C. The spectroscopic data are analogous to those of the product prepared according to Example 1.

EXAMPLE 3

Preparation of Diallylaminomethane-1,1-diphosphonate 100 g (0.27 mol) of diethyl disodium diallylaminomethane-1,1-diphosphonate are refluxed together with 200 ml of 37% hydrochloric acid for 4 hours. After removal of the solvent, the product is made to crystallize using a 1:1 mixture of ethanol and petroleum ether. 73 g (99.8% of theory) of diallylaminomethane-1,1-diphosphonic acid are obtained. Point of decomposition: 140°-150° C.

EXAMPLE 4

Preparation of a Copolymer of Acrylic Acid with 10% of Diethyl Disodium Diallylaminomethane-1,1-diphosphate 5 g (0.013 mol) of diethyl disodium diallylaminomethane-1,1-diphosponate are dissolved in a mixture of 100 g of water and 20 g of isopropanol and heated to 75° C. while introducing a stream of nitrogen. At this temperature, a catalyst solution comprising 1.5 g of (NH$_4$)$_2$S$_2$O$_8$ in 30 g of water and 45 g of acrylic acid are added dropwise synchronously from two dropping funnels. After the exothermic reaction phase is complete, the reaction mixture is additionally heated at 80° C. for two hours. The colorless 26% polymer solution has an intrinsic viscosity K of 21.

EXAMPLE 5

Preparation of a Copolymer of Acrylic Acid with 20% of Diallylaminomethane-1,1-Diphosphonate 10.0 g (0.037 mol) of diallylaminomethane-diphosphonic acid are dissolved in a mixture of 80 g of water and 40 g of isopropanol and copolymerized as described in Example 4, with 40.0 g (0.56 mol) of acrylic acid. The resulting polymer has an intrinsic viscosity K of 21.

EXAMPLE 6

Preparation of a Copolymer of Acrylic Acid with 20% of Diethyl Dipotassium Diallylaminomethane Diphosphonate 10.0 g (0.025 mol) of diethyl dipotassium diallylaminomethane-1,1-diphosphonate are copolymerized, as described in Example 5, with 40.0 g (0.56 mol) of acrylic acid. The resulting polymer has an intrinsic viscosity of 23.

EXAMPLE 7

Preparation of a Copolymer of Acrylic Acid with Diallylaminomethane-1,1-Diphosphonic Acid Using H$_2$O$_2$ as the Radical Chain Initiator This copolymer is prepared analogously to Example 4 using 1.5 g of H$_2$O$_2$ as the catalyst. The resulting polymer has an intrinsic viscosity K of 19.

EXAMPLE 8

Preparation of a Terpolymer of Acrylic Acid with Maleic Anhydride and Diethyl Disodium Diallylaminomethane-1,1-Diphosphonate 7.5 g (0.02 mol) of diethyl disodium diallylaminomethane-1,1-diphosphonate and 20.25 g (0.02 mol) of maleic anhydride are dissolved in a mixture of 120 g of water and 60 g of isopropanol, and the mixture is heated to 80° C. while passing a stream of nitrogen through it. At this temperature, a catalyst solution comprising 2.25 g of (NH$_4$)$_2$S$_2$O$_8$ in 45 g of water and 47.25 g (0.66 mol) of acrylic acid are added dropwise synchronously from two dropping funnels. After the exothermic reaction phase is complete, stirring at 80° C. is continued for 4 hours. The resulting polymer has an intrinsic viscosity K of 23.

EXAMPLE 9

Preparation of a Terpolymer of Methacrylic Acid with 2-Acrylamido-2-Methylpropanesulfonic Acid and Diallylaminomethane-1,1-Diphosphonic Acid 5 g (0.018 mol) of diallylaminomethane-1,1-diphosphonic acid are dissolved in a mixture of 60 g of water and 40 g of isopropanol and the mixture is heated to 80° C. while passing a stream of nitrogen through it. At this temperature, a solution of 5 g of 2-acrylamido-2-methylpropanesulfonic acid and 40 g of methacrylic acid in 20 g of water and a catalyst solution comprising 1.5 g of (NH$_4$)$_2$S$_2$O$_8$ in 30 g of water are added dropwise in parallel from two dropping funnels over a period of 2 hours. After the exothermic reaction phase is complete, the mixture is additionally heated at 80° C. for 3 hours. The resulting polymer has a K value of 26.

EXAMPLE 10

Preparation of a Copolymer of Acrylic Acid with Diallylaminomethane-1,1-Diphosphonic Acid Having a High K Value 5 g (0.018 mol) of diallylaminomethane-1,1-diphosphonic acid are dissolved in 100 g of water and copolymerized at 50° C., as described in Example 4, with 45 g (0.63 mol) of acrylic acid. A colorless 34% polymer solution is obtained. The copolymer has an intrinsic viscosity K of 50.

Examples for practical application:
1. Scale inhibition barium sulfate

The scale-inhibiting effect is demonstrated by means of a tube plugging test. The principle of this test is to monitor the pressure build-up caused by deposition of solids inside a thermostated capillary through which a liquid flows. The apparatus selected is a commercial one from S.B. Systems, Aberdeen, of the PMAC type.

To test for prevention of barium sulfate deposits, the following solutions are mixed:

| | |
|---|---|
| Solution 1: | 74.92 g/l of NaCl |

| | |
|---|---|
| | 0.93 g/l of $Na_2SO_4$ |
| | 2.35 g/l of $NaHCO_3$ |
| Solution 2: | 70.09 g/l of NaCl |
| | 1.21 g/l of $BaCl_2$ |
| | 1.93 g/l of $CaCl_2 \times 2H_2O$ |
| | 3.81 g/l of $MgCl_2 \times 6H_2O$ |

The two solutions are pumped through a stainless steel capillary of inner diameter of 1.1 mm with continuous mixing in a mixing section by means of a hose pump. A sensitive pressure sensor records the increase in pressure in the capillary temperature-controlled at 70° C.

After waiting for a slight increase to about 0.2 bar in order to effect deposition of a small amount of barium sulfate on the steel surface, the inhibitor-free solution 1 is rapidly replaced by an inhibitor-containing solution of the same composition. If the pressure remains constant, it is concluded that inhibition of $BaSO_4$ deposition has been successful. If the pressure increases, the amount of inhibitor or, if the concentration is the same, the type of inhibitor is insufficient for preventing scale formation. Thus, for rating effectivity, the minimum concentration of inhibitor which only just prevents deposition was taken.

In comparative experiments, the following gradations were observed using this process:

In the tables below a +++ sign indicates successful inhibition of scale formation and a --- sign accordingly non-inhibition of scale.

| | Amount of inhibitor (without solvent) | | | | |
|---|---|---|---|---|---|
| Product | 30 ppm | 20 ppm | 17.5 ppm | 15 ppm | 10 ppm |
| Example 4 | +++ | +++ | --- | --- | --- |
| Example 5 | +++ | +++ | +++ | --- | --- |
| Example 6 | +++ | +++ | +++ | +++ | --- |

The compounds according to the invention exhibit an effect against barium sulfate scale deposits even at low concentration.

2. Scale inhibition calcium carbonate

To test for prevention of calcium carbonate deposits, the following solutions are mixed:

| | |
|---|---|
| Solution 1: | 23.0 g/l of NaCl |
| | 2.14 g/l of $CaCl_2 \times 2H_2O$ |
| | 0.38 g/l of $MgCl_2 \times 6H_2O$ |
| | 0.84 g/l of KCl |
| Solution 2: | 23.0 g/l of NaCl |
| | 5.0 g/l of $NaHCO_3$ |

The two solutions are continuously pumped through a mixing cell and then through a stainless steel capillary of inner diameter 1.1 mm by means of a hose pump. A sensitive pressure sensor recorded the increase in pressure in the capillary temperature-controlled at 80° C.

After waiting for an increase to about 0.2 bar in order to effect deposition of a thin calcium carbonate film on the steel surface, the scale inhibitor is continuously metered into the mixing cell via a second pump. If the recorded pressure remains constant, it is concluded that inhibition of $CaCO_3$ deposition has been successful. If the pressure increases, the amount of inhibitor or, if the concentration is the same, the type of inhibitor is insufficient for preventing scale formation. Thus, for rating effectivity, the minimum concentration of inhibitor which only just prevents deposition is taken.

In comparative experiments, the following gradations are observed using this process:

| | Amount of inhibitor (without solvent) | | | | | |
|---|---|---|---|---|---|---|
| Product | 20 ppm | 15 ppm | 12 ppm | 10 ppm | 8 ppm | 6 ppm |
| Example 4 | +++ | +++ | +++ | +++ | --- | --- |
| Example 5 | +++ | +++ | +++ | +++ | +++ | +++ |
| Example 6 | +++ | +++ | +++ | +++ | +++ | --- |
| Example 9 | +++ | +++ | --- | --- | --- | --- |

The compounds according to the invention exhibit an effect against calcium carbonate deposits at low concentrations.

Remarkably, the higher effectivity, resulting from these tests, of the claimed class of compound, compared with the commercial products, in preventing deposits is not only obtained with barium sulfate but also calcium carbonate deposits. This fact is of particular importance, since both types of scale can occur jointly, specifically in sea water injection in crude oil deposits, for example in the North Sea.

3. Calcium-binding power and calcium dispersion

The experimental results using a $Ca^{2+}$-sensitive electrode (buffer: 0.03N $NH_4Cl$ + 0.07 N $NH_3$) give, after extrapolation of the measuring curves to $C_{Polymer}=0$, the following binding constants:

| | mmol $Ca^{2+}$/g of Polymer |
|---|---|
| Example 5 | 4.3 |
| Example 8 | 4.5 |
| Comparative example | 4.0 |

The copolymers according to the invention bind $Ca^{2+}$ better than sodium polyacrylate (MW=27,000) measured as comparison.

The dispersion of calcium carbonate is determined by the filtration method. $CaCO_3$ is precipitated in the presence of the polymer to be tested (test conditions, 4 mmol of $CaCl_2$, 4.4 mmol of $Na_2CO_3$, 2 mmol of NaOH, 250 ppm of polymer, 40° C.) and the amount of calcium passing through a filter is determined.

| | mmol of $Ca^{2+}$/g of Polymer |
|---|---|
| Example 5 | 97% |
| Example 8 | 97% |
| Comparative example | 90% |

Also with respect to calcium dispersing power, the polymers according to the invention exhibit better properties than sodium polyacrylate (MW about 27,000) measured for comparison.

We claim:

1. A copolymer comprising 0.1-50 mol %, of at least one alkenylaminoalkane-1,1-diphosphonate unit of the formula I

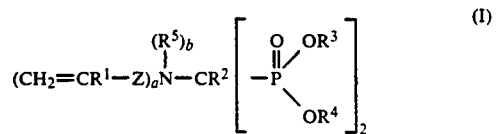

in which
R[1] is hydrogen or methyl,
R[2] is hydrogen or $C_1$-$C_{10}$-alkyl, $R^3$ is $C_1-C_4$-alkyl, phenyl, hydrogen or a cation,
$R^4$ is hydrogen or a cation,
$R^5$ is $C_1-C_{22}$-alkyl, $C_3-C_{22}$-alkenyl,
Z is $C_1-C_3$-alkylene and
a is 1 or 2, b is 0 or 1, a+b is 2,
and 99.9–50 mol % of at least one unit of the formula II $$R^6R^7C=CR^8-Y \qquad (II)$$

in which
$R^6$ and $R^7$, independently of one another, are hydrogen, phenyl or a group of the formula COOM,
$R^8$ is hydrogen, methyl, phenyl or a group of the formula $-CH_2-COOM$,
Y is a group of the formula COOM or
$R^7$ and $R^8$ together are a group of the formula $-C(O)-O-C(O)-$ or
$R^7$ and Y together are a group of the formula $-C(O)-O-C(O)-$ or
$R^8$ and Y together are a group of the formula $-CH_2-C(O)-O-C-(O)-$ and in which
M is hydrogen, lower alkyl or a cation, with the proviso that the monomers of the formula II contain one or two units of the formula $-C(O)-O-$ and contain 0 to 10 mol % of further ethylenically unsaturated monomer units.

2. A copolymer as claimed in claim 1, which contains, as monomer of the formula I, diallylaminomethanediphosphonic acid and/or diethyl disodium diallylaminomethane diphosphonate and/or diethyl dipotassium diallylaminomethane diphosphate incorporated by polymerization.

3. A copolymer as claimed in claim 1, which contains, as monomers of the formula II, acrylic acid, methacrylic acid, maleic acid, maleic anhydride, itaconic acid and/or a lower alkyl ester thereof incorporated by polymerization.

4. The copolymer as claimed in claim 1, wherein there is 1–15 mol % of at least one alkenylaminoalkane-1,1-diphosphonate unit of the formula I and there is 99 to 85 mol % of at least one unit of formula II.

5. The copolymer as claimed in claim 4, wherein $R^3$ and $R^4$ independently of one another are cations which are selected from the group consisting of sodium, potassium and ammonium.

6. The copolymer as claimed in claim 5, wherein M is a cation selected from the group consisting of sodium, potassium and ammonium.

7. The copolymer as claimed in claim 6, wherein $R^5$ is propenyl.

8. The copolymer as claimed in claim 1, wherein $R^3$ and $R^4$ independently of one another are cations which are selected from the group consisting of sodium, potassium and ammonium.

9. The copolymer as claimed in claim 1, wherein M is a cation selected from the group consisting of sodium, potassium and ammonium.

10. The copolymer as claimed in claim 1, wherein $R^5$ is propenyl.

11. A process for the preparation of a copolymer as claimed in claim 1, which comprises polymerizing 0.1 to 50 mol % of a monomer of the formula I with 99.9 to 50 mol % of a monomer of the formula II and, if desired, 0 to 10% mol of a further ethylenically unsaturated monomer in water and/or in a water-miscible solvent, if desired with the addition of a regulator, in the presence of a radical chain initiator at temperatures of 20° to 100° C.

12. The process as claimed in claim 6, wherein the polymerization is at temperatures in the range of 40° to 80° C.

13. The process as claimed in claim 12, wherein the total monomer concentration is 10 to 60% by weight, relative to the total weight of the reaction batch.

14. The process as claimed in claim 11, wherein the total monomer concentration is 1 to 60% by weight relative to the total weight of the reaction batch.

15. The process as claimed in claim 14, wherein the total monomer concentration is 10 to 60% by weight, relative to the total weight of the reaction batch.

* * * * *